United States Patent [19]

Calos

[11] Patent Number: 4,753,874
[45] Date of Patent: Jun. 28, 1988

[54] RAPID MUTATION TESTING SYSTEM FOR HUMAN CELLS

[75] Inventor: Michele P. Calos, Stanford, Calif.

[73] Assignee: Board of Trustees of the Leland Stanford Junior University, Stanford, Calif.

[21] Appl. No.: 753,007

[22] Filed: Jul. 8, 1985

[51] Int. Cl.$^4$ .................. C12N 1/00; C12N 15/00; C12Q 1/02

[52] U.S. Cl. .......................... 435/6; 435/29; 435/32; 435/34; 435/172.1; 435/317.1; 536/27; 935/24; 935/33; 935/79

[58] Field of Search ............... 435/6, 29, 32, 34, 317, 435/172.1; 536/27; 935/24, 33, 79

[56] References Cited

U.S. PATENT DOCUMENTS 4,486,533  12/1984  Lambowitz ............... 435/68 X

FOREIGN PATENT DOCUMENTS 0105149   4/1984  European Pat. Off. ......... 435/172.1
3312928  11/1984  Fed. Rep. of Germany ... 435/172.1

OTHER PUBLICATIONS

Seidman, M. M., et al., "A Shuttle Vector Plasmid . . . ", Gene 38, 233–237 (1985).
Calos, M. P., et al., "High Mutation Frequency in DNA . . . ", Proc. Natl. Acad. Sci USA 80, 3015–3019 (May 1983).
Razzaque, A., et al., "Rearrangement and Mutagenesis . . ., ", Proc. Natl. Acad. Sci., USA 80 3010–3014 (May 1983).
Lebkowski, J. S. et al., "Transfected DNA is Mutated . . . Human Cells", Mol. Cell. Biol. 4(10), 1951–1960 (Oct. 1984).
Sarkar, S., et al., "Error–Prone Mutagenesis Detected in Mammalian Cells by a Shuttle Vector . . . ", Mol. Cell. Biol. 4(10), 2227–2230 (Oct. 1984).

Primary Examiner—Sidney Marantz
Assistant Examiner—Richard Wagner
Attorney, Agent, or Firm—Bertram I. Rowland

[57] ABSTRACT

Mutagenic capability is determined by employing a shuttle vector having prokaryotic and eukaryotic origins, a prokaryotic marker an a gene capable of screening or selection in a prokaryote. The method involves introducing the vector into mammalian cells, exposing the cells to the candidate to be tested for mutagenicity for a time sufficient to allow lesions to occur, rescuing the vector by transforming into a prokaryotic host and screening for mutations of the gene.

13 Claims, No Drawings

RAPID MUTATION TESTING SYSTEM FOR HUMAN CELLS

The U.S. Government has a a paid-up license in this invention and the right in limited circumstances to require the patent owner to license others on reasonable terms as provided for by the terms of Grant No. CA-33056 awarded by the NIH.

BACKGROUND OF THE INVENTION

1. Field of the Invention

In a complex industrial world, the human population is subjected to a continuously changing environment. Many of the physical and chemical components of the environment can affect the accuracy of replication of the genome of host cells. There is substantial concern with mutagenic agents in the environment, due to the established relationship between mutagenesis and carcinogenesis.

In many situations, it would be desirable to have a rapid simple screening procedure which would provide for a mutagenicity index. Such in index would allow for a comparison between various compounds as to their ability to cause lesions in a DNA sequence. In this manner, one could screen a large number of compounds and obtain a value for the mutagenic capability, which could serve as a characteristic of any physical or chemical component of the environment which might induce lesions.

Any system which is employed must take into consideration background values, resulting from spontaneous mutations or mutations which might result from complex interactions of the component of interest with the medium or other factor involving mutagenesis. Therefore, it is not sufficient that one has a system which allows for detection of DNA lesions, but rather one must show that the lesions which can be detected are a specific characteristic of the component being tested. Furthermore, it is desirable, if not necessary, that the agent be tested under conditions as closely tracking the naturally-occurring conditions, as possible.

2. Brief Description of the Relevant Literature

Calos et al., Proc. Natl. Acad. Sci. USA (1983) 80:3015–3019 describes the use of a lacI gene of *E. coli* to score mutation in mammalian cells. Lebkowski et al., Molec. Cell. Biol. (1984) 4:1951–1960 describes the uses of papovavirus-based shuttle vectors containing the bacterial lacI gene to demonstrate mutation frequency in transfected COS7 and CV-1 simian cells, NIH 3T3, 3T6, L and C127 mouse cells and human 293 and HeLa cells. Razzaque et al. Proc. Natl. Acad. Sci. USA (1983) 80:3010–3014, report employing galK as a marker for detecting lesions resulting from transfection into SV40 permissive cells. Yates et al. Proc. Natl. Acad. Sci USA (1984) 81:3806–3810 reports a replication system from EBV which provides episomal maintenance in a human EBV transformed cell. See also, Yates et al. Nature (1985) 313:812–815 which references are incorporated herein by reference.

SUMMARY OF THE INVENTION

Mutagenicity of physical or chemical factors is determined by employing shuttle vectors capable of replication in a prokaryotic host and a mammalian host cell. The shuttle vectors are further characterized by having a marker which allows for selection in a prokaryotic host and a gene which provides for detection of lesions in the gene when expressed in a prokaryotic host. The number of clones which indicate the presence of a lesion in the gene employed for scoring mutagenicity can then be determined for the environmental factor. The method also allows for a rapid method for determining the nature of the lesion.

DESCRIPTION OF THE SPECIFIC EMBODIMENTS

Methods and compositions are provided for scoring the mutagenic potential of environmental factors. The method employs a shuttle vector having replication capability in a prokaryotic host and a mammalian cellular host, particularly human, a marker for selection in a prokaryotic host and a gene employed for scoring as a result of the formation of lesions in the gene. Since human cells are of primary interest and the systems have been developed for human cells, human cells will be employed as paradigmatic. It is to be understood that following the strategies of the subject invention, systems can be developed for other mammals of interest. In referring to humans or human cells, it is intended that human cells and viruses be representative of other mammals.

The method involves introducing vector DNA into human cells capable of being maintained in a viable state in vitro for at least about 24 hours, growing the cells for a sufficient period of time for mutagenesis to occur in the presence of the environmental factor(s), transferring the shuttle vector from the human host to a competent prokaryotic host, and growing the prokaryotic host under selective conditions for the marker and scoring lesions occurring in the gene employed for the scoring of mutagenic potential.

Further details of the nature of the lesions can be obtained. By selecting for lesions involving point mutations, the nature of the point mutation can be determined by transforming the mutated DNA into nonsense suppressor mutant hosts. Mutations generating a nonsense codon are identified as transitions or transversions. This system has been established for the lacI gene. All base pair substitutions are identified except the A:T to G:C transition.

The various components of the method will be considered first. The first component to be considered is the shuttle vector. The shuttle vector will be comprised of replication systems or origins which allow for replication in prokaryotes and human cells. For the most part, prokaryotic replication systems will be obtained from plasmids and viruses, so that the shuttle vector will survive as an episomal element in the prokaryotic host. A large number of plasmids and viruses are known which can be used in a variety of prokaryotic hosts. Illustrative plasmids include pBR322, pSC101, pACYC184, pRK290, pML, etc. Viruses are also a source of replication systems, particularly such viruses as lambda, P1, M13, etc.

Desirably, the replication system will provide for a copy number of at least five, preferably at least ten, but should not be greater than about 500 or more, where the replication of the plasmid may result in a substantial reduction in viability of the prokaryotic host.

For the most part, the replication systems for human cells will come from viruses, such as papovavirus (e.g. SV-40), Epstein-Barr virus (origin and EBNA gene), or adenovirus, with the Epstein-Barr virus replication system preferred. While a chromosomal replication system may be employed, these have not been developed and will usually limit the copy number.

Where the replication system requires additional genetic elements other than the origin, such as the T antigen of simian virus-40, such genetic capability may be provided in the host genome or with a helper plasmid or any other system which provides the necessary genetic capability. One replication system may be selected over another, particularly where it is found that the entire system minimizes spontaneous mutagenesis. Thus, there will be preferred combinations of replication systems and hosts, e.g., Epstein-Barr virus and human lymphoid cells and SV40 and 293 cells. The copy number for human cells is analogous for prokaryotic cells, preferably the copy number being at least 50, more preferably at least 100.

The shuttle vector will have at least one marker and may have two markers or more. Markers will be preferably chosen to allow for selection, rather than screening, although screening is permissible, but not convenient. Markers of interest may be bactericide resistant genes, such as genes which provide for resistance to antibiotics, e.g., kanamycin, ampicillin, chloramphenicol, tetracycline, penicillin, etc., metallothioneins, which provides for resistance to heavy metal toxins, or the like. Alternatively, genes may be employed which provide prototrophy to an auxotrophic host. Various genes include leu, trp, his, pro, or the like, that is, genes usually involved with production of an essential metabollite, such as amino acids.

The marker which is selected will be chosen in accordance with the prokaryotic host, since the marker must be effective in allowing for selection of prokaryotic hosts which have the shuttle vector, as distinct from those prokaryotic hosts which lack the shuttle vector. Therefore, employed hosts will be deficient in the phenotypic trait provided by the marker.

The mutational target or scoring gene will be required to have a number of desirable characteristics. First, prokaryotic hosts must be available which allow for detection of the scoring gene. Thus, hosts must be capable of being maintained in a viable state in the absence of the scoring gene. Therefore, genes associated with lethal mutations will generally be avoided. Second, desirably the gene will allow for screening, rather than selection. That is, the gene will directly or indirectly provide a product which can be readily detected, particularly by a visible characteristic, typically a product which provides for a colored clone, colored environment or other visible characterisic, e.g., clone shape or size. For a colored clone, the gene will normally code for a product which is part of a system which results in a colored product, e.g., an enzyme for which a substrate can be provided which provides a colored product or a gene which acts as a repressor or activator of another gene which provides the enzyme. Alternatively, a tRNA gene may be employed, where because of the small size of the gene, the gene can be sequenced or the gene may be part of a system, e.g., a suppressor gene, which provides for a detectable phenotype.

Third, the gene must have a sequence which undergoes a reasonable rate of mutagenesis, so that a broad range of values will be available in evaluating environmental components for mutagenic potential. Desirably, scoring will be as a result of lesions which result in an absence of function of any expression product of the scoring gene, or other scoring techniques can be employed. However, where a visual result is obtained, due to the presence or absence of a function of the expression product, the assay is more rapid and can be carried out more efficiently and economically.

A system which can be used involves a structural gene associated with lactose metabolism. One gene of particular interest is the LacI gene which acts as a repressor of the $\beta$-gal gene. This system has a number of merits, since one can provide that the $\alpha$ portion of $\beta$-galactosidase is encoded for on the shuttle vector, while the terminal portion of $\beta$-galactosidase may be produced on a different episomal element or in the chromosome. The $\alpha$-complementation system is desirable, because if an $i^-z^+$ host is used, blue colonies could appear due to a spontaneous plasmid curing within a colony. In this manner, curing of the plasmid resulting in an appearance of $i^+$ is avoided.

Another system which may be employed is the galK system. GalK codes for galactokinase. Mutants for galK can be detected since they grow on plates containing 2-deoxygalactose. Mutants can be confirmed by streaking in MacConkey agar with galactose.

Other systems include use of a suppressor tRNA gene. Mutation in the tRNA gene would cause failure of production of an enzyme, such as $\beta$-galactosidase. When the enzyme is coded by a gene containing a nonsense mutation, the unmutated tRNA will suppress the nonsense mutation to provide an active enzyme product. Mutation resulting in a non-functional tRNA will have the effect of a non-functional enzyme gene.

The shuttle vector will generally be under about 40 kb, preferably under about 30 kb, and more preferably under about 20 kb, usually exceeding about 5 kb.

Each of the genes to be expressed will have the appropriate transcriptional and translational initiation and termination regulatory signals.

Once the shuttle vector has been devised, it may be introduced into a human cell. Depending upon the vector and host cell system which is employed, the host may be a relatively short lived cell, having a half-life of less than six months, frequently less than one month, or, for the purposes of the invention, may be immortal. With a relatively short half-life, the cells will usually be transformed just prior to the exposure to the mutagen but at least for a sufficient time for the vector to enter the nucleus. In this situation, a relatively large background is created by the mutations resulting from the introduction of the vector DNA into the host.

Contrastingly, where an immortalized cell line containing the vector is employed, the cell lines can be screened for the absence or substantial absence of mutations in the scoring gene and that cell line maintained, providing for a substantially reduced mutation background.

A wide variety of human cell lines may be employed, where the human cell allows for a sufficient period of growth in culture. Therefore, the cells may or may not be immortalized, usually being immortalized, by such techniques as mutagenesis, employing a transforming virus, employing a naturally-occurring tumor cell, which is established in culture, or other convenient techniques. Different tumor cells may be used with advantage, particularly, since there is an interest in having a host cell which minimizes background mutagenesis or lesion formation. Illustrative host cells include HeLa, 293, Mo, KG-1, EBV transformed lymphoid cells, V-266, etc. The cells may be lymphocyte cells, mammary cells, embryonic lung cells, fetal cells, embryonic kidney cells, epithelial cells, lymphoid cells, myeloid cells, or the like. Various viruses which may be used for transformation or have effected transformation in the established strain naturally include Epstein-Barr virus, adenovirus, SV-40 HCLV-I, HTLV-II or the like.

The shuttle vector may be introduced into the mammalian host by any convenient means, such as transformation, transfection, or the like. Various techniques include calcium phosphate precipitate-mediated transfection (Wigler et al. Cell (1977) 11:223–232, DEAE dextran procedure (McCutchan and Pagano, J. Natl. Cancer Inst. (1968) 41:351–356), or the like. After introduction of the shuttle vector into the human host, the system is now ready for detection of mutagenicity or lesion formation of an environmental component. The shuttle vector may exist in the human cell as an episomal element or integrated into the chromosome.

The cells are grown in an appropriate liquid nutrient medium, e.g., DMEM containing from about 10 to 15% fetal calf serum. Alternatively, the cells may be plated onto a solid agar containing nutrient medium and grown to at least about 40% confluency, generally from about 50 to 70% confluency. After at least about 12 hours, usually about 24 hours, the mutagenizing agent or combination of mutagenizing agents are applied, which may be applied at various application levels, e.g., concentrations, energy levels, etc. in relation to the levels to which human cells may be exposed. Normally, the cells will be maintained in the nutrient medium for at least about 24 hours, preferably for about 48 hours, while exposed to the test component(s). In some situations it may be desirable to expose the bare DNA to the mutagenic agent to determine its in vitro effect.

After having grown the human cells, the plasmids are then rescued into an appropriate prokaryotic host by conventional techniques. Prokaryotic hosts are chosen for the analysis which provide minimal background mutagenesis, that is, they provide a low level of spontaneous mutations during the screening of the plasmids.

The plasmid DNA may be isolated in accordance with the Hirt procedure (J. Mol. Biol. (1967) 26:365–369), although any procedure may be employed, such as those procedures described in Maniatis et al. A Laboratory Manual, CSHL, Cold Spring Harbor, N.Y. (1982). The plasmid DNA may then be transformed into the prokaryotic host. See, for example, Lebkowski et al., supra. The clones of the host may then be grown on an appropriate medium. Where the shuttle vector allows for direct detection, for example, with the lacI gene, employing 5-bromo-4-chloro-3-indolyl-$\beta$-D-galactoside as the $\beta$-gal substrate, those shuttle vectors having an I$^-$ mutation will give rise to blue colonies. Thus, by determining the ratio of white colonies to blue colonies, a mutagenicity value can be defined. With other markers of mutagenicity, different detection techniques can be employed. Of course, in some situations, it may be desirable to obtain a more detailed determination of the nature of the lesions. In these situations, whole plasmids or restriction enzyme digests may be employed, either on the entire genome or isolated plasmid DNA. With restricted DNA, by employing probes, one can detect insertions or deletions. For point mutations, sequencing would be appropriate or one may use prokaryotic hosts having a suppressor background to detect point mutations generating a nonsense codon.

The scoring gene can be investigated for point mutations employing the following procedure. Conveniently, the gene can be rescued into episomal elements having copies of the gene with varying deletions about 10 to 20 base pairs apart. A series of hosts are provided, each one carrying the gene with a particular deletion. The site of the point mutation can be detected where a functional gene occurs with the next successive deletion, but not the previous deletion. By then transforming the mutated DNA into suppressor tRNA backgrounds, with knowledge of the region of the point mutation, one can define the particular mutation in relation to the suppressor tRNA(s) which provide a functional gene.

By following the above procedure, one can rapidly detect the efficiency of mutagenesis of a physical or chemical component on human cells in culture. By employing compounds which have previously been evaluated by a variety of techniques, one can relate the values and experience obtained with the present method with the prior art methods, so that a more accurate evaluation of the transforming or mutagenizing capability of a compound may be determined.

The subject invention can be used in an alternative way in screening cells for defective correction systems. Cells from patients suspected of having a defective correction system or other genetic defection which results in an elevated level of genetic lesions could be screened. The cells would be transformed with the appropriate shuttle vector which would then be rescued into bacteria and analyzed. If appropriate, the host cells could be immortalized prior to transfection with the shuttle vector, employing oncogenes, fusion or viruses for immortalization. Diseases associated with defective DNA repair systems include xeroderma pigmentosum, and Bloom's syndrome. These cells could also be used to evaluate agents for mutagenicity, providing for enhanced stress.

The following examples are offered by way of illustration and not by way of limitation.

EXPERIMENTAL

All references cited are incorporated herein for the purpose indicated in the description.

Materials and Methods

Vector DNA. The plasmid pJYMib (Lebkowski et al. Mol. Cell Biol. (1984) 4:1951–1960) was used as the shuttle vector. pJYMib contains all of SV40, pML (a pBR322 derivative), the entire lacI gene, and the amino-terminal portion of lacZ.

pJYMib was prepared as follows. pMC9 was used as a source of a 1.7 kb lac fragment which included the lacI gene. A I$^-$ missense mutation, T63, which removes the single cutting side for HincII within lacI was crossed onto the lacI-containing plasmid pMC1 (Calos, Nature (1978) 274:762–765). A 1.7 kb HincII fragment of pMC1 T63 now contains all of lacI, the lac control region and the beginning of lacZ, up to the HincII site corresponding to amino acid 146 of $\beta$-galactosidase. The I$^Q$ promoter mutation carried by the T63 donor episome may have also been transferred to the plasmid during the cross. The 1.7 kb lac HincII fragment was isolated from pMC1 T63 and EcoRI linkers were attached to it. After restriction with EcoRI, the fragment was ligated to the EcoRI site of pBR322. The correct recombinant was identified as a red colony on MacConkey lactose plates upon transformation into strain CSH35, $\Delta$(lacproB) supE thi F' lacI$^S$ proB) Miller (1972) Experiments in Molecular Genetics, Cold Spring Harbor Laboratory Press, Cold Spring Harbor, N.Y.).

The plasmid pMC9 T63 was returned to an I+ state by transforming it into strain GM1, araΔ(lacproB) thi F' lacproB I$^Q$L8 (Miller et al. (1978) in: Miller and Reznikoff (eds) The Operon, Cold Spring Harbor Laboratory Press, Cold Spring Harbor, N.Y., pp. 31–88) to allow recombination with the I+ episome. The I+ pMC9 was isolated by transforming plasmids grown in GM1 into strain Δ196, ara val Δ(lacproB) galE strA thi (φ80dlac ΔlacI tonB trp (Schmeissner et al. J. Mol. Biol. (1977) 109:303–326). When plated on agar containing X-gal (5-bromo-4-chloro-3-indolyl-β-D-galactoside), an I+ plasmid will give a white colony in the I−Z+ Δ196 background.

The i+ 1.7 kb EcoRI fragment was excised from pMC9 employing EcoRI, purified and inserted into a partial EcoRI digest of pJYM, which contains all of the SV40 virus in the BamHI site of pML (Luskey and Botchan, Nature, London (1981) 293:79–81) to provide pJYMib. pJYMib has the lacZ fragment oriented closer to SV40 than the lacI gene.

Plasmid DNA was prepared by the alkaline lysis procedure and purified on cesium chloride gradients (Maniatis et al. (1982) Molecular Cloning, A Laboratory Manual, Cold Spring Harbor Laboratory, Cold Spring Harbor, N.Y.). The frequency of I− mutants after pJYMib DNA is transformed directly into *E. coli* is approximately $1 \times 10^{-5}$.

Transfection. The human cell line 293 (a human embryonic kidney line transformed with adenovirus-5 (Graham et al. J. Gen. Virol. (1977) 36:59–72)) was employed for transfection and grown in Dulbecco modified Eagle minimal essential medium (DMEM) supplemented with 10% fetal calf serum. Cells were plated in 60 mm dishes the day before transfection such that they were approximately 40% confluent at the time of transfection. Calcium phosphate-mediated transfection was done with two μg of plasmid DNA per plate without carrier DNA, according to the procedure of Wigler et al. Cell (1977) 11:223–232, except that the coprecipitates were left on the cells overnight.

Mutagenesis. Fourty-eight hours after transfection the cells were exposed to UV light. The medium was aspirated off the plates and the top cover removed. UV light was administered from above using a germicidal lamp at an incident rate of 0.55 J/m$^2$ per second. The UV dose was calibrated with a model 1L254 International Light photometer. Mutation collection was done at a dose of 50 J/m$^2$.

Detection of I− mutants. Plasmid DNA was extracted from the 293 cells by the Hirt procedure (J. Mol. Biol. (1967) 26:365–369). The extracted DNA was treated with DpnI (Boehringer Mannheim) to remove bacterial input DNA (Lebkowski et al. Mol. Cell Biol. (1984) 4:195–1960.) The DNA was transformed into a recA− derivative of *E. coli* MC1061 F'150 kan (Miller et al. EMBO J. (1984) 3:3117–3121) and I− colonies were scored as blue colonies on plates containing X-gal (Calos et al. Proc. Natl. Acad. Sci. USA (1983) 80:3015–3019; Lebkowski et al. Mol. Cell Biol. (1984) 4:1951–1960). Plasmids from I− bacterial colonies were purified by the alkaline lysis procedure (Birnboim and Doly, Nucleic Acids Res. (1979) 7:1513–1523). Plasmid DNA was digested with EcoRI and run on agarose gels as described by Calos et al. (1983) supra., to determine the nature of the I− mutations.

In order to assure that the DNA is in the nucleus, mutagenesis is done 24 to 48 hours after transfection. In order to fix mutations and amplify I− molecules, the vectors are allowed to remain in the human nucleus for a further one to two days, while exposed to the mutagenic agent. Colonies receiving an I− plasmid are blue while I+ colonies are white. Tens of thousands of colonies are obtained from each 60mm dish of human cells, so relatively rare mutations can readily be found. Operation of the lacI shuttle without external mutagenesis results in a spontaneous I− frequency of $3.5 \times 10^{-4}$ or 0.035% (247 I− colonies among 706,841 colonies examined). This frequency is 35 times the mutation frequency of pJYMib transformed directly into *E. coli* without passage through the human cells, which is approximately $1 \times 10^{-5}$. It is also 1 to 2 orders of magnitude higher than the mutation frequency expected for a chromosomal mammalian gene. However, it is substantially below the mutation frequencies reported for shuttle vectors in other types of mammalian cells. These frequencies are typically in the range of 1%. (Calos et al. (1983) supra.; Lebkowski et al. Mol. Cell Biol. (1984) supra.)

Transfected 293 cells were exposed to increasing doses of UV light and the resulting I− frequencies were determined after rescue of vector DNA. The dose response curve over a range of 0 to 70 J/m$^2$ of UV light was roughly linear and resulted in an approximately 4-fold I− frequency. Where the I− mutations were examined, it was found that the percentage of point mutations had increased from 70% to approximately 90% (197 of 221). Therefore, the frequency of deletions with and without UV was unchanged at approximately 0.01% ($1 \times 10^{-4}$). The frequency of point mutations increased 5-fold with UV light, going from 0.025% to 0.13%. A UV dose of 50 J/m$^2$ induces approximately 50% killing of the cells during the course of the experiment and a depression in the number of *E. coli* colonies obtained of approximately 10-fold.

To demonstrate that the mutations were not the result of UV damage in the DNA which was processed to mutations in *E. coli*, vector DNA was irradiated in vitro with 10–100 J/m$^2$ and transformed into the recA− bacterial recipient. A sharp drop in colony number was observed but no noticeable increase in mutation frequency was observed.

To obtain the sequence of a sizeable number of UV-induced point mutations, a large collection of I− mutants generated in 293 cells irradiated with 50 J/m2of UV light 48 hours after transfection was assembled. A similar collection of spontaneous I− mutants was assembled from cells which had not received UV light. The I− mutants from each plate of 293 cells were examined by EcoRI digestion to identify putative point mutations. One or a few point mutation candidates obtained from each plate of 293 cells were analyzed further. The mutations were first crossed by genetic recombination from the pJYMib plasmid to an F'lacproB episome. Each I− episome was then transferred to a series of nonsense suppressor strains (Coulondre and Miller, J. Mol. Biol. (1977) 117:577–606) and the mutations that generated a nonsense codon were identified. Seventy of the 245 UV-induced I− mutations analyzed yielded a nonsense codon. Similarly, 61 of the 229 spontaneous I− point mutations generated a nonsense condon. The high fraction of nonsense mutations (28–30%) found among the putative point mutations indicates that the majority of the mutations placed in this class are base substitutions.

Each nonsense mutation was assigned to one of the amber, ochre, or UGA mutations at 69 different sites of lacI using a combination of deletion mapping and an analysis of the pattern of nonsense suppression (Coulondre and Miller (1977), supra.) Since the wild-type DNA sequence of lacI and the sequence of each nonsense codon is known, assignment of the position of the nonsense codon unambiguously identifies the DNA sequence change involved in each mutation.

The UV-induced spontaneous mutations show a pattern dominated by the G:C to A:T transition, which accounts for 42 of the 54 mutations. Of these mutations, 38 out of 42 (90%) occur at pyrimidine-pyrimidine sequences. Several of the sites have mutated more frequently than others. Nine G:C to T:A transversions and one A:T to T:A transversion were also detected. The system employed does not detect A:T to G:C transitions.

The subject system provides a rapid and powerful analytical system. Large collections of mutations can conveniently be analyzed rapidly by simple screening, employing a label which allows for visual or automated detection. Large samples can be obtained so as to minimize coefficients of variation. The technique is relatively rapid and simple so as to minimize technician involvement.

Although the foregoing invention has been described in some detail by way of illustration and example for purposes of clarity of understanding, it will be obvious that certain changes and modifications may be practiced within the scope of the appended claims.

What is claimed is:

1. A method for determining mutagenicity of a suspected mutagenizing agent which comprises:
    contacting a mammalian cell host, having a low background of spontaneous mutagenesis and carrying a shuttle vector in the nucleus, with said mutagenizing agent for a time sufficient to permit point mutations to occur,
    said shuttle vector characterized by:
    (a) a first replication system functional in said mammalian cell host;
    (b) a second replication system functional in a prokaryotic host;
    (c) a marker for selection of a prokaryotic host comprising said shuttle vector; and
    (d) a DNA sequence which allows for rapid detection of point mutations in said sequence;
    rescuing said shuttle vector into a prokaryotic host after said time; and
    growing said prokaryotic host under selective conditions for said marker and analyzing for the presence of a point mutation in said DNA sequence.

2. A method according to claim 1, wherein said analyzing includes determining at least in part the nature of the lesion.

3. A method according to claim 1, wherein said DNA sequence is the prokaryotic lacI gene.

4. A method according to claim 1, wherein said mammalian cell is a human cell.

5. A method according to claim 4, wherein said human cell is immortal.

6. A method for detecting mutagenicity of a suspected mutagenizing agent which comprises:
    contacting a human cell host having a low background of spontaneous mutagenesis and carrying a shuttle vector in the nucleus with said mutagenizing agent for a time sufficient to permit point mutations to occur;
    said shuttle vector characterized by:
    (a) a first replication system which is an SV40 or EBV replication system;
    (b) a second replication system function in E. coli;
    (c) a marker for selection of an E. coli host comprising said shuttle vector; and
    (d) a structural gene encoding for prokaryotic lacI;
    rescuing said shuttle vector into E. coli after said time; and
    growing said E. coli under selective conditions for said marker and analyzing for the presence of a point mutation in said lacI gene, wherein said human cell host carrying said shuttle vector is obtained by transforming said shuttle vector into said human cell host and screening transformed cells for the absence of mutations in the marker gene.

7. A method according to claim 6, wherein said first replication system is EBV and said human cell is an immortalized cell.

8. A method according to claim 6, wherein said first replication system is SV40 and said human cell is strain 293.

9. A method according to claim 6, wherein said analyzing includes determining at least in part the nature of the lesion.

10. A plasmid under 40 kb comprising a first prokaryotic replication system, an EBV replication system, a marker for selection in a prokaryotic host, a DNA sequence coding for a protein associated with lactose metabolism.

11. A human cell carrying a plasmid according to claim 10.

12. A plasmid according to claim 10, wherein said sequence is the lacI gene.

13. A human cell carrying a plasmid according to claim 12.

* * * * *